United States Patent [19]

Doyle et al.

[11] Patent Number: 4,635,289

[45] Date of Patent: Jan. 6, 1987

[54] METHOD AND APPARATUS FOR INSPECTING PRINTED WIRING BOARDS

[75] Inventors: Keith G. Doyle; Roy A. Lloyd, both of Sunbury-on-Thames, England

[73] Assignee: Lloyd Doyle Limited, Surrey, England

[21] Appl. No.: 633,436

[22] Filed: Jul. 23, 1984

[30] Foreign Application Priority Data

Jul. 25, 1983 [GB] United Kingdom ............... 8320016

[51] Int. Cl.$^4$ ............................................. G06K 9/00
[52] U.S. Cl. ........................................ 382/8; 356/431
[58] Field of Search ...................... 382/8, 22; 356/431

[56] References Cited

U.S. PATENT DOCUMENTS

| | | | |
|---|---|---|---|
| 4,037,941 | 7/1977 | Belleson et al. | 350/285 |
| 4,242,662 | 12/1980 | Tsujiyama et al. | 382/8 |
| 4,479,145 | 10/1984 | Azuma et al. | 382/8 |
| 4,500,202 | 2/1985 | Smyth | 382/8 |
| 4,541,114 | 9/1985 | Rutenbar et al. | 382/8 |
| 4,570,180 | 2/1986 | Baier et al. | 382/8 |

FOREIGN PATENT DOCUMENTS

2700252  7/1978  Fed. Rep. of Germany .......... 31/28

OTHER PUBLICATIONS

Procedings of the Fourth International Joint Conference on Pattern Recognition–Nov. 1978, Kyoto, JP; N. Goto et al, "An Automatic Inspection System for Mask Patterns", pp. 970–974.

Primary Examiner—Anthony V. Ciarlante
Attorney, Agent, or Firm—Walter C. Farley

[57] ABSTRACT

Apparatus for testing a printed wiring board comprising means for optically scanning a board to be tested in two orthogonal, X-Y axes such that for each scan in the Y direction it scans a narrow strip of the board of predetermined width, w in the X direction. The optical scanning means is arranged to provide n.m discrete signals for each scan in the Y direction, wherein n is a predetermined number of signals representative of characteristics of the board across the width w of the strip (typically 1000) and m is a number dependent upon the dimension of the board to be scanned in the Y direction. Processing means is provided for processing the signals in groups of n'×m' where n' is less than or equal to n and m' is less than or equal to m (typically n' and m' are 40) to provide signals representative of the characteristics of the board along said strip and for storing said signals. Control means is arranged to cause the scanning means repeatedly to scan the board in the Y direction and to step it a predetermined amount in the X direction at the end of each scan until a required area of the board has been scanned and the processing means has processed a plurality of said groups of signals. The processing means is further arranged to identify common areas of each conductive track such that at the completion of a test, the storage means contains information representative of the X-Y coordinates of a plurality of datum areas and of the said datum areas which are interconnected. The datum areas may be holes, edge connectors, pads and the like. The processing means also comprises means for comparing the stored signals with a plurality of signals representative of the required interconnections for the board (the required wiring list) thereby to test the quality of the board.

38 Claims, 18 Drawing Figures

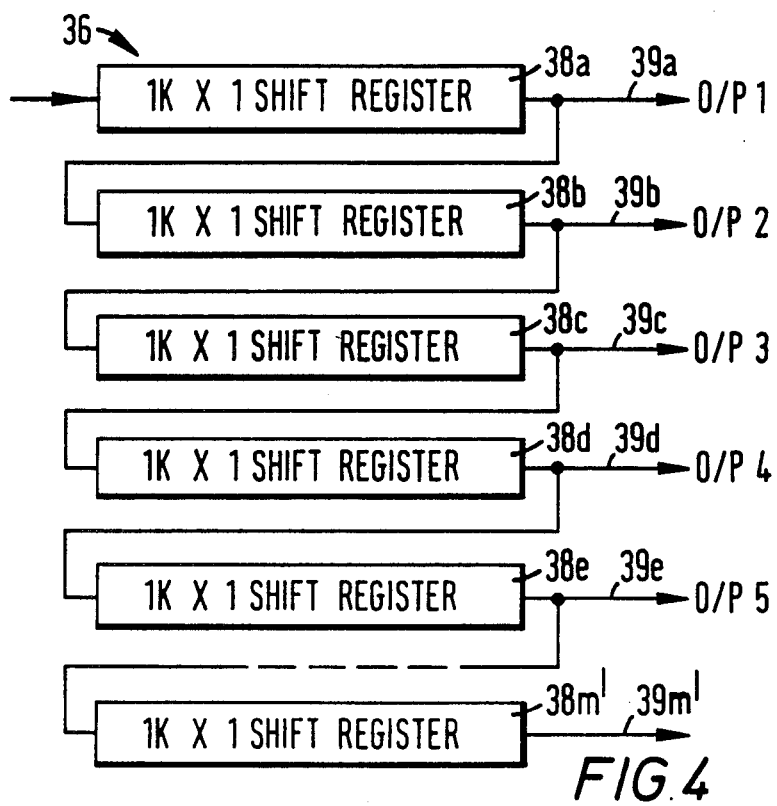

KEY:-
0 = NON-TRACK  :  X = LABEL UNKNOWN  :  A = ALLOCATION REQUEST

| OBTAINED FROM EDGE RAM → | | | | | | | | | | | |
|---|---|---|---|---|---|---|---|---|---|---|---|
| 27 | X | X | 0 | 0 | X | X | 0 | 0 | X | X | 0 |
| 27 | 27 | 0 | 0 | 35 | 35 | 0 | 0 | 46 | 46 | 0 | 0 |
| | | | | | | | | 0 | 31 | 31 | 0 |

FIG. 8 ORIGINAL DATA.   ← PREVIOUS SCAN LINE
→ SCAN DIRECTION

| 27 | X | X | 0 | 0 | X | A | 0 | 0 | X | X | 0 |
|---|---|---|---|---|---|---|---|---|---|---|---|
| 27 | 27 | 0 | 0 | 35 | 35 | 0 | 0 | 46 | 46 | 0 | 0 |
| | | | | | | | | 0 | 31 | 31 | 0 |

FIG. 9 AFTER FIRST SCAN.
← SCAN DIRECTION

| 27 | 27 | 0 | 0 | 35 | 0 | 0 | 57 | 0 | 46 | 46 | 0 |
|---|---|---|---|---|---|---|---|---|---|---|---|
| 27 | 27 | 0 | 0 | 35 | 35 | 0 | 0 | 46 | 46 | 0 | 0 |
| | | | | | | | | 0 | 31 | 31 | 0 |

FIG. 10 AFTER SECOND SCAN.
↑ SCAN DIRECTION

| 27 | 27 | 0 | 0 | 35 | 35 | 0 | 57 | 0 | 46 | 46 | 0 |
|---|---|---|---|---|---|---|---|---|---|---|---|
| 27 | 27 | 0 | 0 | 35 | 35 | 0 | 0 | 46 | 46 | 0 | 0 |
| | | | | | | | | 0 | 31 | 31 | 0 |

FIG. 11 AFTER THIRD SCAN.
→ SCAN DIRECTION

METHOD AND APPARATUS FOR INSPECTING PRINTED WIRING BOARDS

This invention relates to a method and apparatus for inspecting a pattern on a substrate such as a pattern on a printed wiring board.

In the manufacture of printed wiring boards it is important to ensure not only that the printed wiring is complete and to the required layout or pattern but also to ensure that it meets certain specified criteria, for example that the width of the printed wiring conductor does not fall below a predetermined minimum value and that the spacing between adjacent conductors does not fall below another predetermined value, either of which can result in a substandard printed circuit board which is liable to fail in use after manufacture.

A reduction in the effective width of a printed wiring conductor can be caused by a nick or pinhole in the conductor at a point or points along the conductor as well as by a length of narrow conductor due to faulty processing or design.

The simplest boards can be inspected visually but for more complex broads this is difficult, time consuming and expensive.

One well known apparatus for testing boards electrically is the tracking or "bed or nails" tester. Such apparatus can check the continuity between the various connection points on a board but is unable to detect nicks, pinholes, regions of narrow track, or partial bridges which can occur if the spacing between adjacent conductors is too small. Such apparatus also require expensive tooling to enable them to be used in the inspection of a wide range of boards. It is also known to scan printed wiring boards optically, and to process the resulting data electronically to detect defects. Systems have been devised which can operate in either a "comparison" or a "non-comparison" mode. To operate by comparison with a known good board on a pixel-by-pixel basis requires precise alignment of the two boards and the optics, unless the system is to be limited to detecting very coarse defects. Systems which operate in a "non-comparison" mode use feature detection to identify parts of the board which do not conform with what is expected from a normal interconnection pattern. They have very high "false alarm" rates as they will respond incorrectly to features such as lettering or small defects which do not affect the funcsionality of the board.

According to the invention there is provided apparatus for testing a printed wiring board comprising means for optically scanning a board to be tested in two orthogonal, X-Y axes such that for each scan in the Y direction it scans a narrow strip of the board of predetermined width, w, in the X direction, the scanning means being arranged to provide n.m discrete signals for each scan in the Y direction, wherein n is a predetermined number of signals representative of characteristics of the board across the width w of the strip and m is a number dependent upon the dimension of the board to be scanned in the Y direction, and processing means for processing the signals in groups of $n' \times m'$ where $n' <= n$ and $m' <= m$ to provide signals representative of the characteristics of the board along said strip and means for storing said signals, control means arranged to cause the scanning means repeatedly to scan the board in the Y direction and to step it a predetermined amount in the X direction at the end of each scan until a required area of the board has been scanned and the processing means has processed a plurality of said groups of signals, the processing means being further arranged to identify common areas of each conductive track such that at the completion of a test, the storage means contains information representative of the X-Y coordinates of a plurality of datum areas and of the said areas which are interconnected.

The datum areas may comprise conductive material surrounding holes in the board such that at the end of a test the stored information is equivalent to a wiring list of interconnected datum areas.

The datum areas may comprise edge connector areas.

The processing means may comprise means for comparing the stored signals with a plurality of signals representative of the required interconnections for the board (the required wiring list) thereby to test the quality of the board.

The apparatus may comprise track contraction means for processing preselected areas of each group of $n1 \times m1$ signals in such a manner as to determine whether the width of a conductor at any point along it's length is less than a predetermined minimum width.

The apparatus may further comprise track expansion means arranged to process the scanned signals in such a manner as to determine whether the spacing between adjacent conductors at any point along their length is less than a predetermined value.

One embodiment of the invention will now be described by way of example with reference to the accompanying drawings, in which:

FIG. 4 is a simplified representation of a multiple delay circuit for use in the apparatus of FIG. 1.

FIG. 5 is a part of a table showing the outputs of the circuits of FIG. 4.

FIGS. 8 to 11 are tables for use in describing the operation of an interconnection analyser.

Figure 1:
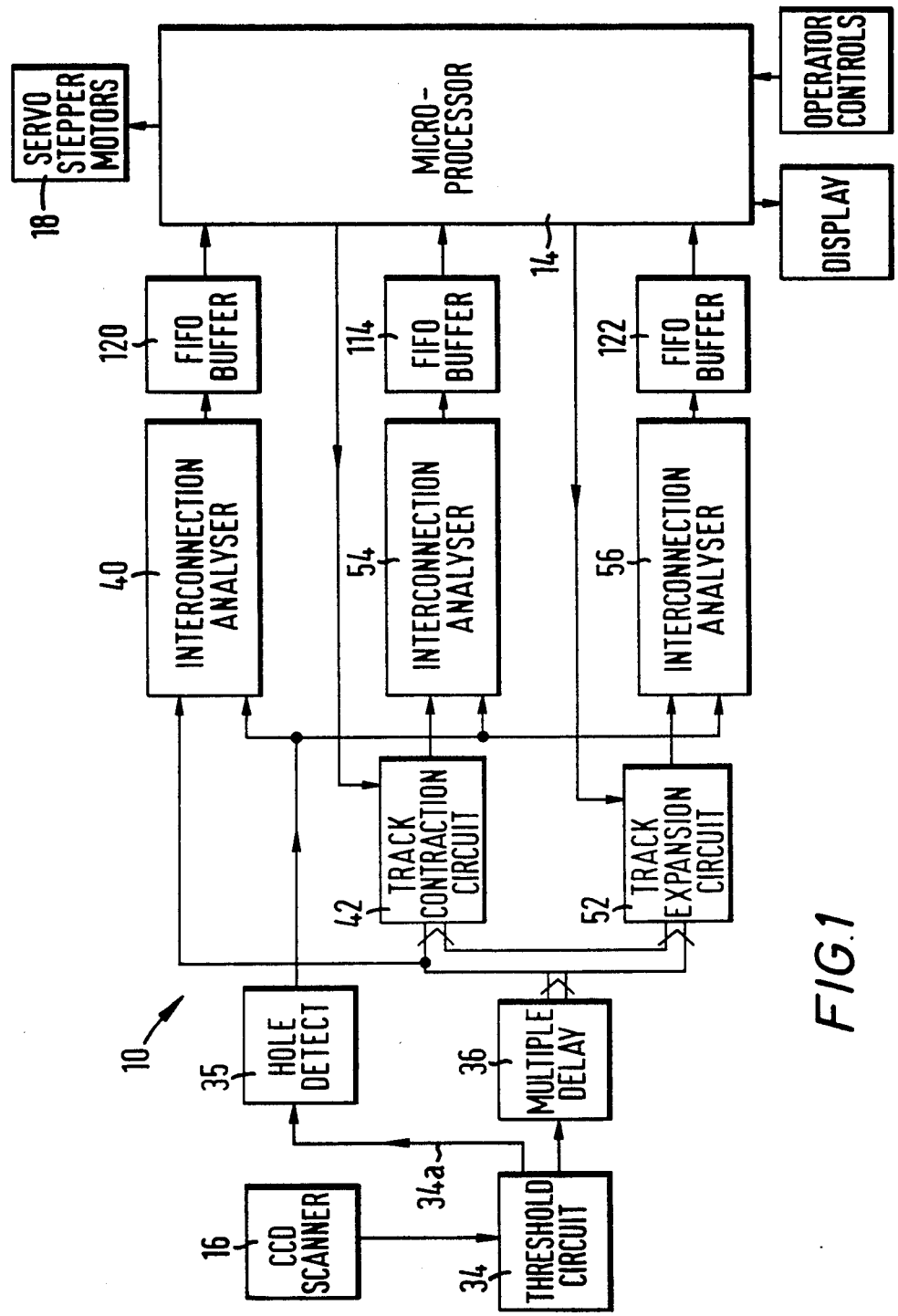
FIG. 1 is a block schematic diagram of an apparatus according to the invention for testing a printed wiring board.
Figure 2:
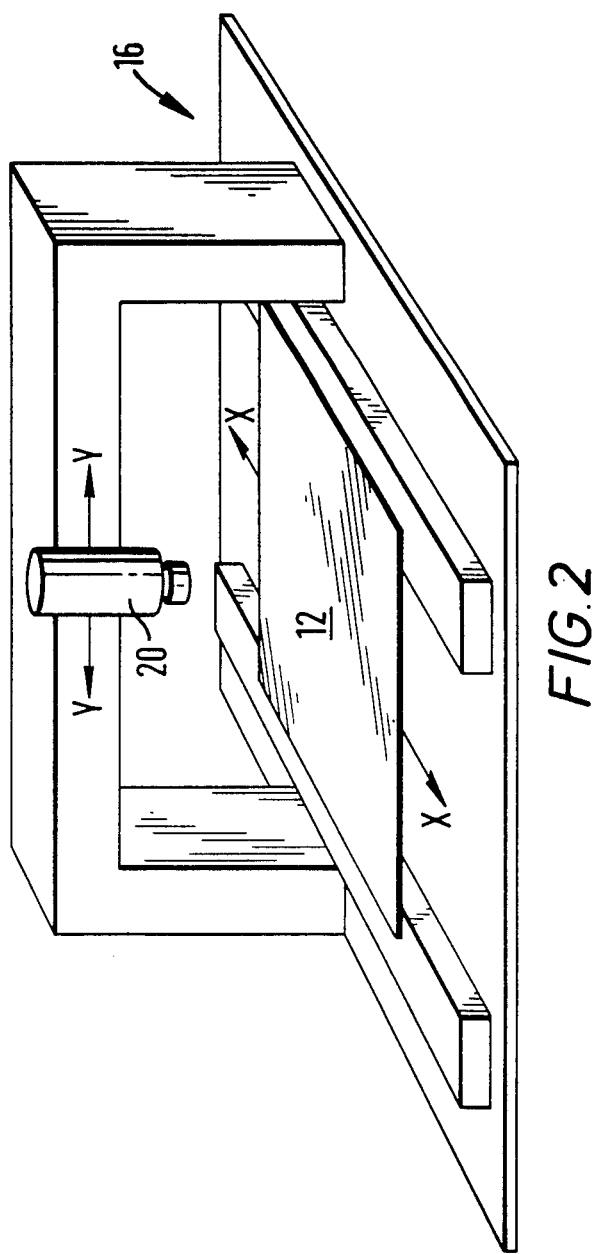
FIG. 2 is a simplified, perspective view of a scanning means suitable for use with the apparatus of FIG. 1.
Figure 3:
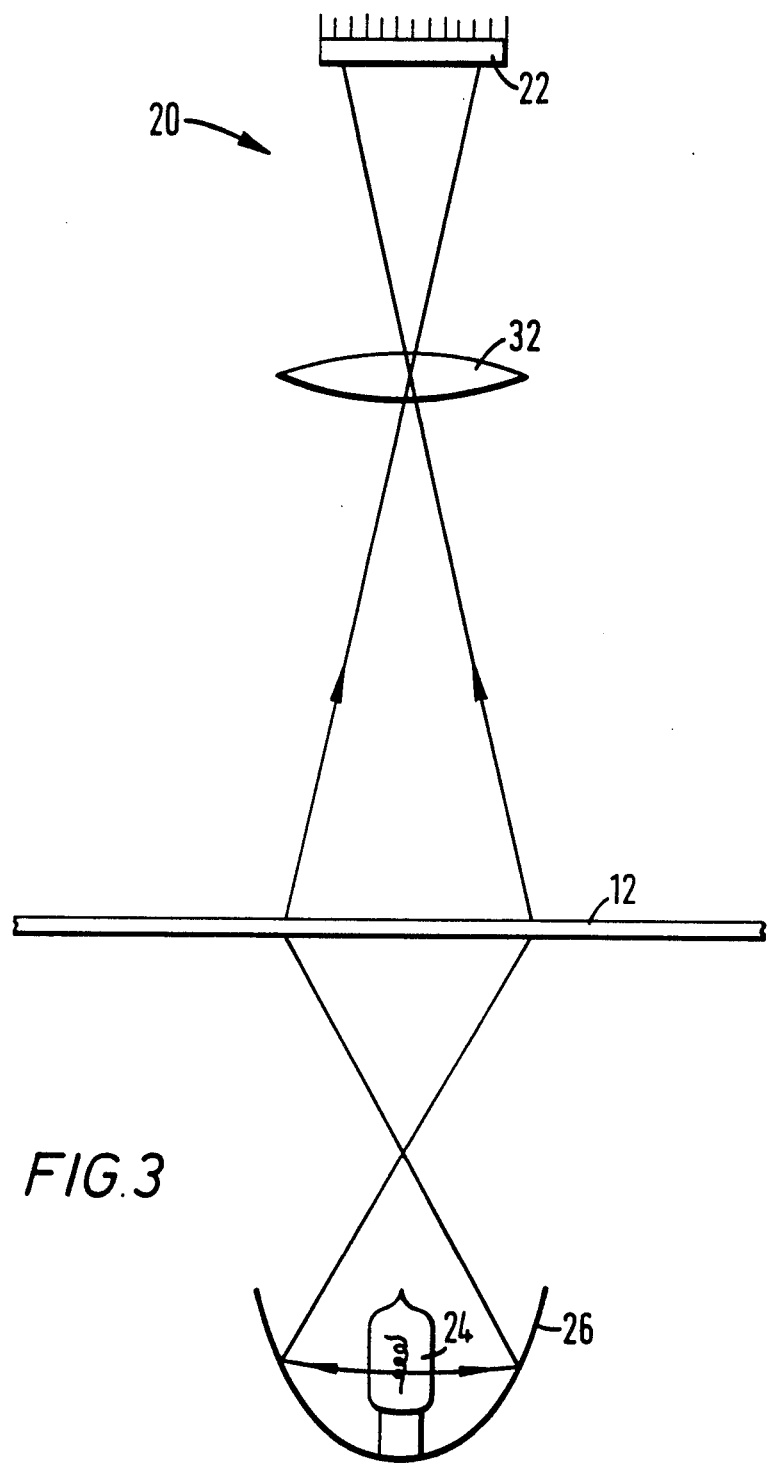
FIG. 3 is a simplified view of an optical arrangement and an optical scanning device suitable for use with FIGS. 1 & 2.

Refering to the drawings, in FIG. 1 there is shown an apparatus 10 for testing the wiring of a printed wiring board 12 (FIGS. 2 & 3).

The apparatus 10 is controlled by a microcomputer 14 which also includes various storage elements such as random access memories (RAM's) for use in the operation of the apparatus and the storage of information for use in testing a board 12.

The apparatus 10 comprises an optical scanner 16 which is controlled by servo/stepper motors 18 to traverse backwards and forwards across the surface of the board 12 in the Y direction and after each traversal it is moved relative to the board a predetermined distance in the X direction.

FIG. 2 shows a simple arrangement for such a scanner 16, in which the optical scanning device 20 can be traversed backwards and forwards in the Y direction while the board 12 can be stepped a discrete distance in the X direction between each Y traversal. Other arrangements are of course possible, for example the board 12 could be moved on an X-Y table moveable in both orthogonal axes with the device 20 fixed in position or the board 12 could be mounted in a fixed position and the scanning device 20 mounted for movement in the X-Y directions.

FIG. 3 shows a simplified side view of an optical scanning device 20, utilising a charge coupled device (CCD) camera 22 such as one sold by Fairchild under type No. CD1300R.

Light from a tungsten-halogen lamp 24 is concentrated by an ellipsoidal reflector 26 onto the underside of the board. The light reaches the board at a very wide range of angles, and can diffuse quite a long way sideways, so that power supply tracks on the board 12, for example do not completely block out the rear illumination.

Large ground planes will do so, but this effect can be eliminated by designing them as a grid with a hole or holes in, which does not significantly affect the electrical performance.

Alternatively the board 12 could be scanned with a retroreflective scanner using either conventional tungsten-halogen or laser light and the reflected light detected to distinguish track areas from non-track areas and from holes without changing any of the principles herein described.

The front surface of the board is imaged by a standard camera or enlarger lens 32 onto a charge-coupled device 22, which contains a linear array of photosites together with circuitry for reading out the light levels from each photosite.

In this embodiment there are 1024 photosites arranged to scan a strip about 20 mm wide in the X direction as the board 12 is scanned in the Y direction, ie each photosite is responsive to a 20 micron×20 micron area (a pixel).

Thus the linear array of photosites effectively produces a parallel output containing 1024 analogue pieces of information in the X direction. As the board is scanned in the Y direction the array continues to develop 1024 output signals at discrete positions 20 microns apart for the complete scan in the Y direction.

The 1024 signals from the CCD scanner device 16 representing a strip 20 mm long in the X direction and 20 microns wide in the Y direction are coupled serially to the input of a dual threshold circuit 34 having a first, lower threshold reference voltage input and a second, higher threshold reference voltage input.

The circuit 34 distinguishes between track (ie conductor), non-track (ie insulating substrate) and holes by comparing each input signal with the two threshold levels. If the input signal from the scanner 16 is less than the first threshold voltage the circuit produces a logic signal '1' indicative of track area on output 34b; if it is greater than the second threshold voltage the circuit 34 produces a logic signal '1' on the output 34a indicative of a hole in the board and if the input signal has a level equal to or between the first and second threshold levels it produces a logic signal '0' indicative of a non-track area on output 34b. These input signals are coupled to the circuit 34 at a 10 MHz clock rate.

The binary stream of information indicative of track and non-track pixel areas appearing at output 34b is fed to a multiple delay circuit 36. The circuit 36 is implemented using random access memories (RAM's) for low cost, but can be considered conceptually, and for ease of description, as a set of shift registers 38 each one of which feeds the next as shown in FIG. 4.

Each shift register 38 is 1024 bits long so that at time t=1024 the first shift register 38a would be regarded as containing a full 1024 bits of information in one 20 mm wide strip of the area being scanned. At time t=2048 the first 1024 bits of information will have been shifted serially into shift register 38b and shift register 38a will contain the next succeeding 1024 bits of information and so on.

As the delay through each shift register is equal to one scan line in the X direction the parallel outputs 39a to 39m' of the shift registers 38a to 38m' at any time can be regarded as m' bits of information in a row in the Y direction of scan. Thus the outputs of the shift registers represent a parallel scan across the width of the scan, as shown in part in the table of FIG. 5.

The parallel output signals from the multiple delay circuit 36, that is the outputs 39a to 39m' are coupled in parallel to a pair of circuits 42, 52 whose function is to determine for each point in the scanned image whether it is within a preset distance of a track or non-track area. The circuit 42 is called a track contraction circuit and the circuit 52 a track expansion circuit; the track expansion circuit 52 is similar to the track contraction circuit 42 with the exception that it's input and output signals are inverted. Any one of the outputs of the multiple delay circuit 36 (for preferance the middle one of the 39a to 39m') is also fed to the interconnection analyser 40.

The interconnection analyser 40, to be described hereinafter, is coupled through a first-in, first-out buffer 120 to the microcomputer 14. It's function is to produce a set of signals to be stored which are a representation of a wiring diagram for the printed wiring board 12, that is it provides a set of X-Y coordinate signals representative of holes in the board and edge connector areas, if any, labelled to indicate which holes/edge connector areas are interconnected.

The track contraction circuit 42 will now be described with reference to FIG. 6. The circuit 42 comprises a plurality of tapped shift registers 44a to 44m' having inputs 45a to 45m' coupled to the outputs 39a to 39m' respectively of the shift registers 38. Each circuit 44 has a programmable, tapped output 46a to 46m' which is coupled to the preset input 47a to 47m' of a presettable down counter 48a to 48m' respectively. The taps on the shift registers 44 are under the control of the microprocessor 14.

In a practical embodiment m'=40 so that there are forty shift registers 38 and 44 and the shift registers 44 are forty bits long (that is n'=40) so that the set of shift registers 44 at any one time contain information equivalent to an area 40×40 bits (or pixels) square, although it will be realised that, in operation, bits of information are being shifted in parallel through the various registers at clock rate. Thus at a given instant the the information contained in the shift registers 44 can be regarded as a digital image of part of the board. The contraction circuit 42 is arranged to determine whether or not all of the bits in the shift registers 44 which would fit in a circle of radius R, and where R is equal to half the minimum specified track width, are a binary '1' to indicate track. The value of R is predetermined for the board 12 and it's value is set into the computer by the operator. For example in the 40×40 matrix of shift registers 44, the value of R could be made equal to 20 and it would be possible to look at the bits of the individual cells of the shift registers to determine their value. If each cell was provided with an output an individual AND gate could be coupled to various cells in a particular shift register and the outputs of the individual AND gates coupled to the inputs of another AND gate so that if, and only if, all of the individual cells contained a binary '1' then the output of the final AND gate would be a '1' to indicate a complete track in the area of radius R. However if only a single cell was set to '0' then the output of the final AND gate would be zero indicating that the track was not entirely complete at the area being tested at that instant in time.

In the example given using forty shift registers, each forty bits long the first and fortieth shift registers could be tapped at, say cells 20 and 21, the middle twentieth and twenty first shift registers could have every cell tapped and connected to an associated input of two forty input AND gates. The shift registers two to nineteen would have progressively more cells tapped and the registers twenty-two to thirty-nine would have progressively fewer cells tapped so that the outputs from the tapped cells would approximate to a circle of radius R. However this arrangement would be expensive in AND gates and quite complex and somewhat difficult to vary in practice and the circuit of FIG. 6 was devised.

Figure 6:
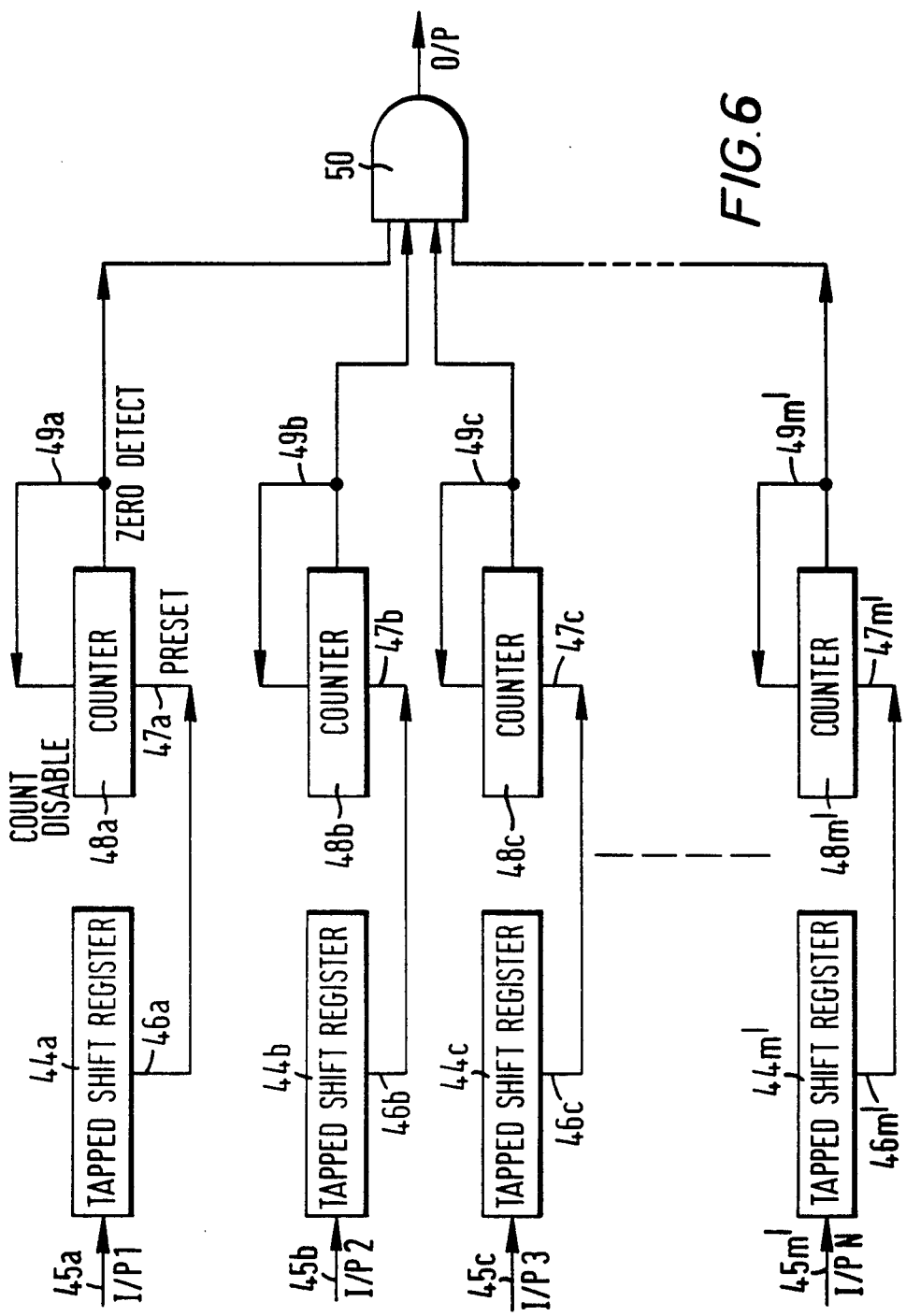
FIG. 6 is a simplified block circuit diagram of a track contraction, or expansion, circuit of FIG. 1.

In FIG. 6 the taps on the shift registers 44 can be set automatically by the microcomputer 14 under the control of the operator and it will be seen that they are variable delays, the delay being a maximum (20 bits) for the first and fortieth shift registers 44 and a minimum (zero) for, say, the twentieth and twenty-first. The delays for shift registers 2 to 19 decrease progressively from 19 to 1 bits and for shift registers 22 to 39 increase progressively from 1 to 19 bits. The counters 48a to 48m' can be present to a count determined by it's position, ie for the first and fortieth counters the preset count would be a minimum value (say 1 or 2) and for the twentieth and twenty-first counters to a maximum value (say 40). The other counters are preset to values increasing and decreasing in the same way as the delays through the shift registers 44 decrease and increase.

Figure 7:
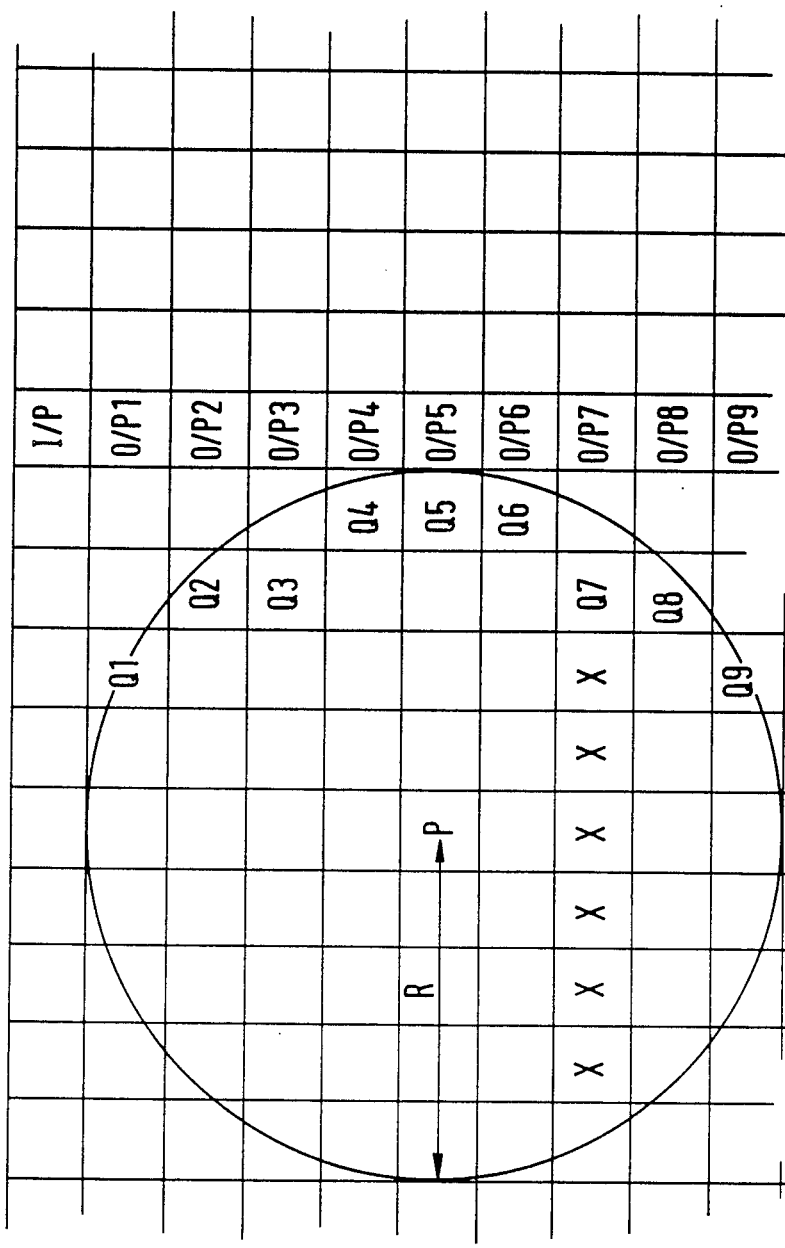
FIG. 7 is a simplified drawing illustrating the processing of a group of $n1 \times m1$ signals by the circuit of FIG. 6.

FIG. 7 is a diagrammatic representation of a simplified circuit of FIG. 6 having nine preset shift registers 44 each nine bits long. At the instant shown in FIG. 7, the circuitry is determining whether there are any non-track areas within a distance R from the point P. Each circuit 44,48 determines whether there are any non-track areas along a corresponding strip such as that marked XXXXXXX and the outputs of all of the counters 48 are combined in AND gate 50 to provide a single output; '1' if all of the counter outputs indicate track; '0' if any one or more of the counter outputs indicate the presence of a non-track area. In the example shown the seventh counter 48g would be preset to a count of seven whenever a non-track element is seen at position Q7. The counter is then counted down to zero so that if all of the elements marked X contain track, ie are at '1' then the output of the counter will go to '1'. This disables further counting of the counter 48g via line 49g until the counter is preset again. The output of AND gate 50 will thus go high '1' if only if all of the elements within a distance R of P contain track. The output of the AND gate is thus a serial representation of an image similar to that arriving at the threshold circuit 34, except that it has been delayed, and the track areas have been "thinned down" in accordance with the minimum track width settings. Thus, if the track is complete but does not meet the minimum track width requirements at any point along it's length, for example if there is a nick or a flaw in it the output of AND gate 50 will go to zero at this point. This information will be processed in an interconnection analyser 54 and the output fed to the microcomputer 14 via a FIFO buffer 114.

The track expansion circuit 52 is similar to the track contraction circuit 42 with the exception that the input to it and the output from it are inverted. It is thus caused to consider track as non-track and vice versa. In this case if the value R is made half the minimum allowable spacing between conductors then if the spacing is adequate the output of it's AND gate (equivalent to AND gate 50) will be a series of '1' s but if the spacing at any position on the board is less than the minimum allowable the output of the AND gate will go to '0'. The information from the track expansion circuit will be processed in an interconnection analyser 56 and the output fed to the microcomputer 14 via the FIFO buffer 122.

The above explanation has been considerably simplified as if the information is static but it should be realised that the information is being shifted through the shift registers at clock frequency and the testing is taking place continuously on the fly.

Also it will be remembered that the image is 1024 bits wide in the X direction and although the delay shift registers 38 are 1024 bits long the shift registers 44 are only n'=40 bits long. Thus at say t=1024 p where p is an integer the circuit 42 may be inspecting rows 1 to 40 in the X direction, at t=(1024 p+1 clock pulse) rows 2 to 41 and so on.

As mentioned the train of output signals from the circuits 42, 52 are processed by interconnection analysers 54, 56 respectively.

The function of the interconnection analyser is to determine which holes, and edge connector areas if any, are connected together to form a wiring list which is stored in the computer. In this embodiment edge connector areas are designated as holes but are identifiable as edge connectors by their X-Y coordinates.

For a good board the wiring lists compiled by the circuits 54, 56 ie the "thinned" and "fattened" images respectively, should be the same but if there are any narrow cuts, nicks, pinholes or inadequate spacing between conductors the two wiring lists will differ. They can also be compared with a wiring list obtained from a photographic or other artwork prepared for the board or from a known good board. Alternatively, or in addition they can be compared with a wiring list prepared from the interconnection analyser 40 which, in effect provides a basic list of the various complete interconnections but regardless of the presence of nicks, pinholes or the like, provided that the circuit is complete and regardless of the spacing between conductors provided that they do not actually touch.

The interconnection analysers 54, 56 scan the data streams from the track contraction circuit 42 and the track expansion circuits 52 respectively and associate a "label" with each track area. These labels are binary numbers which are allocated in sequence whenever a "new" piece of track is scanned. When a hole or termination regarded as a hole is detected in the board, the label of the corresponding piece of track is passed to the microprocessor together with the coordinates of the hole. When two pieces of track which have been given different labels converge, so that they are known to be connected together, the two labels concerned are passed to the microprocessor with the information that they are interconnected. The edge of a band 1024 bits wide × m bits long is defined by the final, or 1024th, bit in each 1024 bits across the width w of the band. The labels for the edge of a band 1024 bits wide being scanned are held in a special store (edge RAM) so that they can be used to relate each band to the next succeeding band adjacent to it. The labelling process is carried out in three stages as illustrated in the tables of FIGS. 8, 9, 10 & 11. In each of these figures, the lower line represents labels that have been determined for the previous scan line, and the upper line represents the labels that have been determined so far for the scan line that is currently being labelled. The data for this scan line is traversed three times before all the labels are correctly allocated. The first traversal is from right to left, and serves only to identify any region of track which does not touch any regions of track in the previous line, and which will therefore require a new label to be allocated to it. In the Figures individual areas of track are allocated a code, in which:

O represents a non-track area.

X represents a track area to which a label is to be allocated.

A represents an area where a label request signal has been generated.

A two digit number e.g. 27 represents a label which has been allocated to a track area.

Refering to FIG. 8. as mentioned the lower line shows part of a scanned line which has been labelled and, reading from left to right, the first track areas have been labelled as track areas 27, from the edge RAM, the next three areas are non-track, the next two areas have been labelled as track areas 35 and so on.

The labels are allocated by a label allocation counter (FIG. 16) and are coupled at 16 bit words to the microprocessor 14 when either a hole or an edge connector on the board 12 are detected, along with the X-Y coordinates of that feature, and when a "collision" (to be defined hereinafter) occurs.

The leftmost digit, 27, is stored in an "edge" RAM which identifies the labels allocated to areas of track along the edge of the previously scanned 20 mm wide band. This facilitates identification of the edges of each subsequent band as it is scanned.

The upper line of FIG. 8 shows the leftmost digit 27 allocated to the first track area, because it represents an edge of the scanning line and could be numbered by reference to the "edge RAM". The remainder of the line merely shows areas of non-track and track to which labels are to be allocated.

The first label allocation traversal is from right to left as shown in FIG. 9 and, as mentioned, serves to identify areas of track which do not touch any areas of track in the lower, immediately proceeding scanned track. If it identifies such track it allocates a label allocation request A in the first non-track area that occurs after that particular piece of track. In FIG. 9 there are two such adjacent areas at positions 10 and 11 from the left. As the data is being traversed from right to left the first available non-track area is position 9 and this is allocated a label allocation request A as shown.

Figure 14:
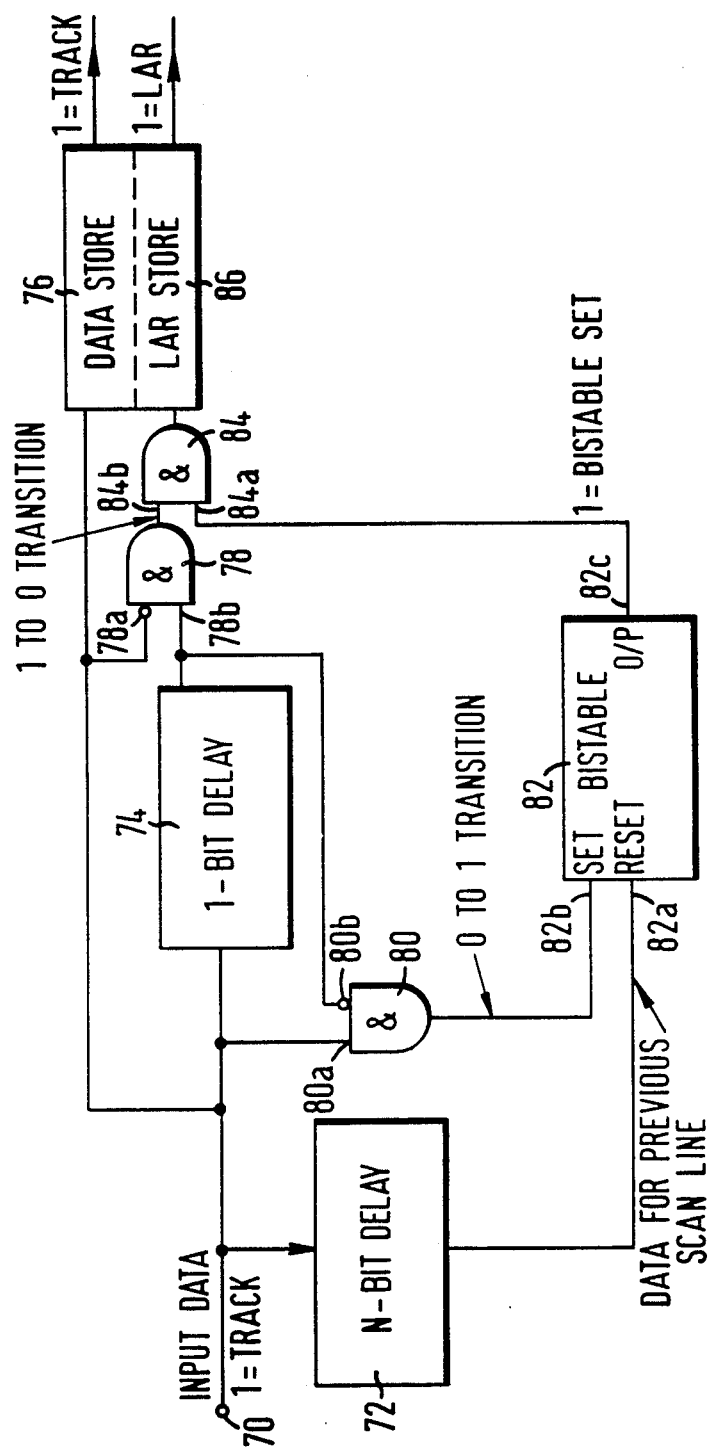
FIG. 14 is a block diagram of a label allocation request generation circuit.

A circuit for performing this function is shown in FIG. 14.

Refering to FIG. 14, input data in serial form and representing the 1024 bits of information of a scanned line is coupled from the output of the track contraction circuit 42 to an input 70 of the interconnection analyser 54. A similar circuit to that of FIG. 14 is used in the interconnection analysers 40 and 56 and so the operation in relation to these circuits will not be discussed in detail.

The stream of data coupled to input 70 is coupled to an n-bit delay 72 (n=1024), a 1-bit delay 74, an n bit data store 76, to the inverting input 78$a$ of an AND gate 78, and to input 80$a$ of an AND gate 80.

The output of the 1024 bit delay 72 and the AND gate 80 are coupled to reset and set inputs 82$a$, 82$b$ of a bistable circuit 82. Thus current data bits corresponding to the track/non-track areas in the upper row of FIG. 9 are coupled to the set input 82$b$ of the bistable circuit 82 and the corresponding data from areas in the previous scan line are fed to the reset input 82$a$ of the bistable circuit 82. So long as the input data is representative of non-track ie '0' the AND gate 80 has a '0' on input 80$a$ and a '0' on the line to input 80$b$ due to the 1-bit delay through delay 74 which is inverted to present a '1' input to the AND gate 80. Thus as soon as a piece of track is encountered the corresponding '1' bit on input 80$a$ causes the AND gate 80 to provide a '1' on the input 82$b$ to set the bistable circuit 82, which provides a '1' at the output 82$c$. If the next piece of input data is a '1' representative of track the input at 80$a$ is a '1' but the previous '1' input delayed 1-bit arrives at the input 80$b$ is inverted and the output of AND gate 80 returns to "zero".

The effect of this is that as soon as a piece of track is encountered at input 70 the output of AND gate 80, is at '1' for one clock pulse duration.

The delay circuit 72 being 1024 bits long is effectively providing information about the area of track immediately below the area currently being examined. If the area in the lower row is also track then a '1' will be applied to the reset input of bistable 82 to reset it's output to '0'. However if the output of the delay 72 is '0' representing non-track then the bistable will remain set and a '1' will be applied to input 84$a$ of AND gate 84. However, while the input 70 is receiving track signals the '1' signals fed to inverting input 78$a$ keep the output of AND gate 78 at '0' and thus inhibit the AND gate 84. As soon as the input reverts to non-track '0' the output of AND gate 78 goes to '1' and a '1' is fed into the 1024 bit allocation request store 86. This '1' bit is fed into store in the first non-track area after the track to non-track transition. For example in FIG. 9 where scanning is taking place from right to left, track is located at position 11 from the left which is not adjacent to a piece of track in the previously scanned lower row and a label must be allocated to it. This '1' coupled to input 80$a$ and the '0' from the 1-bit delay 74 will provide a '1' on the output of AND gate 80 to set the bistable 82. However the AND gate 84 will be inhibited by the corresponding '1' on the inverting input of AND gate 78. The next '1' input at position 10 from the left will be coupled to AND gate 80 but it's output will return to '0' because the previous '1' from position 11 delayed 1-bit in delay 74 will appear at inverting input 80b. Thus bistable 82 remains set but can be reset if a '1' appears at input 82a. At position 9 from the left in FIG. 9 the input signal at 70 reverts to non-track '0' and this coupled to inverting input 78a of AND gate 78 removes the inhibit signal from AND gate 84 and allows a '1' into the label allocation request store 86. This is shown as A in FIG. 9 and as aforementioned appears in the first non-track area after a piece of track to which a label has not been allocated.

Thus the data store 76 contains the 1024 bits of information of the scanned line and the LAR store 86 contains a series of '0' and a '1' at the position immediately to the left of an isolated piece of track to which a label has not been allocated and which is not adjacent to a piece of track in the line previously scanned.

The stores 76, 86 are bidirectional so that data can be read out from left to right during the next traversal (FIG. 10) so that at position 9 from the left a label allocation request is fed from store 86 to a label allocation counter (to be described in relation to FIGS. 12 and 16) which allocate a new label, in this case 57, to the track areas 10 and 11 from the left and updates the label allocation counter to the next label to be allocated.

Also during this traversal from left to right, the track areas are labelled up as far as possible by reference to the labels in adjacent elements. Some elements may be impossible to label at this stage, and they are identified by a special 'Don't Know' code, so that they can be resolved during the third traversal, for example the track at position 6 from the left in FIG. 10 because it is adjacent to an area of non-track in the previous line immediately below it. The labels for the previous scan line are held in a RAM 108 marked RAM 1 in FIG. 15, and the left-right traversal circuit' uses these to generate a set of labels including 'Don't Knows' in the RAM 100 marked RAM 2 in FIG. 15. during the third traversal these values are transferred back to RAM 1 by the 'right-left traversal circuit' FIG. 17 which also replaces any 'Don't Knows' by the correct labels.

Figure 16:
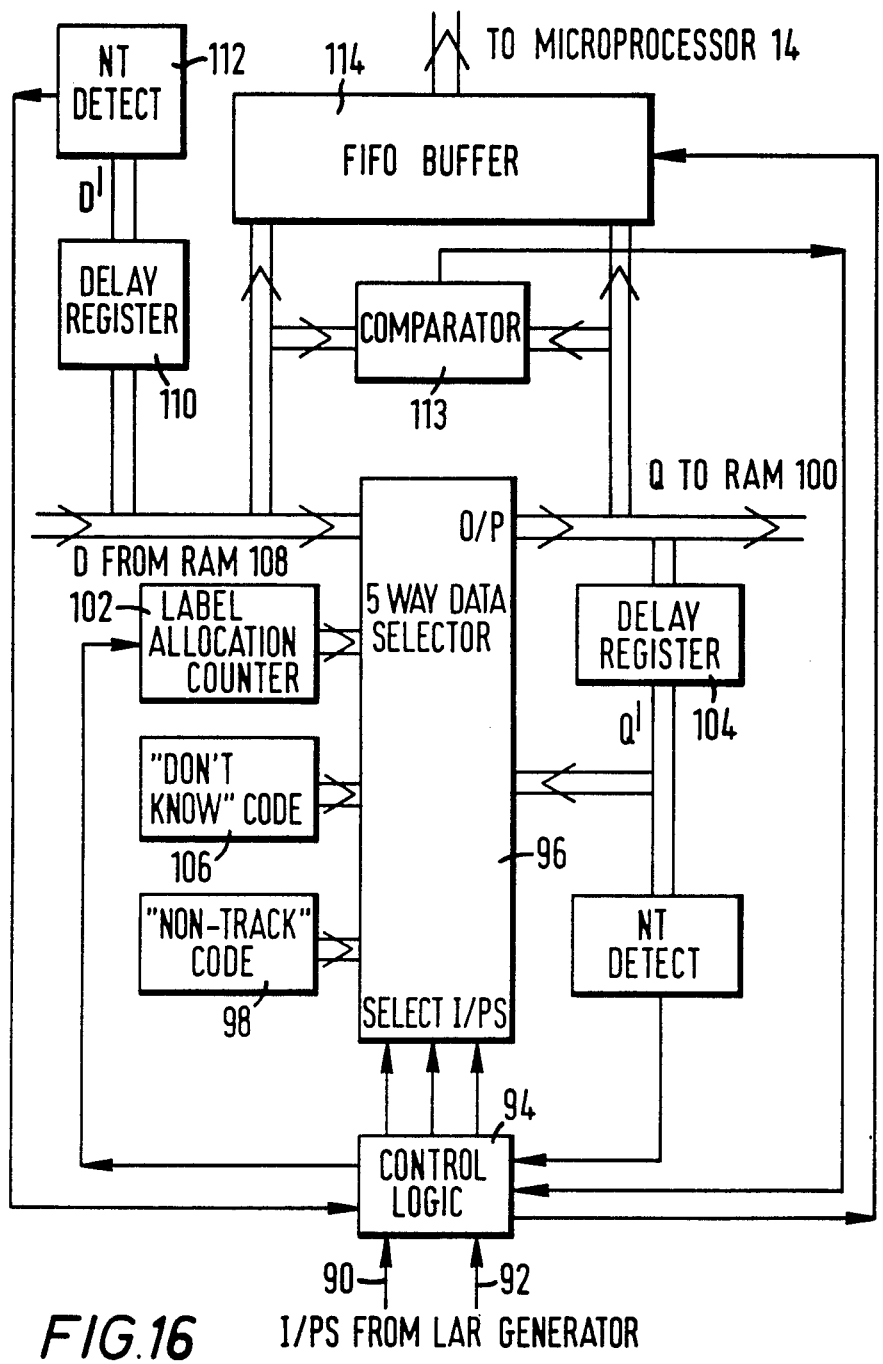
FIGS. 16 & 17 are block diagrams of circuits for use in the circuit of FIG. 15.

The output from the 1,024 bit data store 76, being a series of '0' and '1' representing non-track and track, is coupled to a data input terminal 90 of circuit FIG. 16. Likewise, the output from the label allocation request (LAR) Store 86, being a series of '0' but containing a '1' for each new label to be allocated is coupled to input terminal 92 of FIG. 16.

Figure 12:
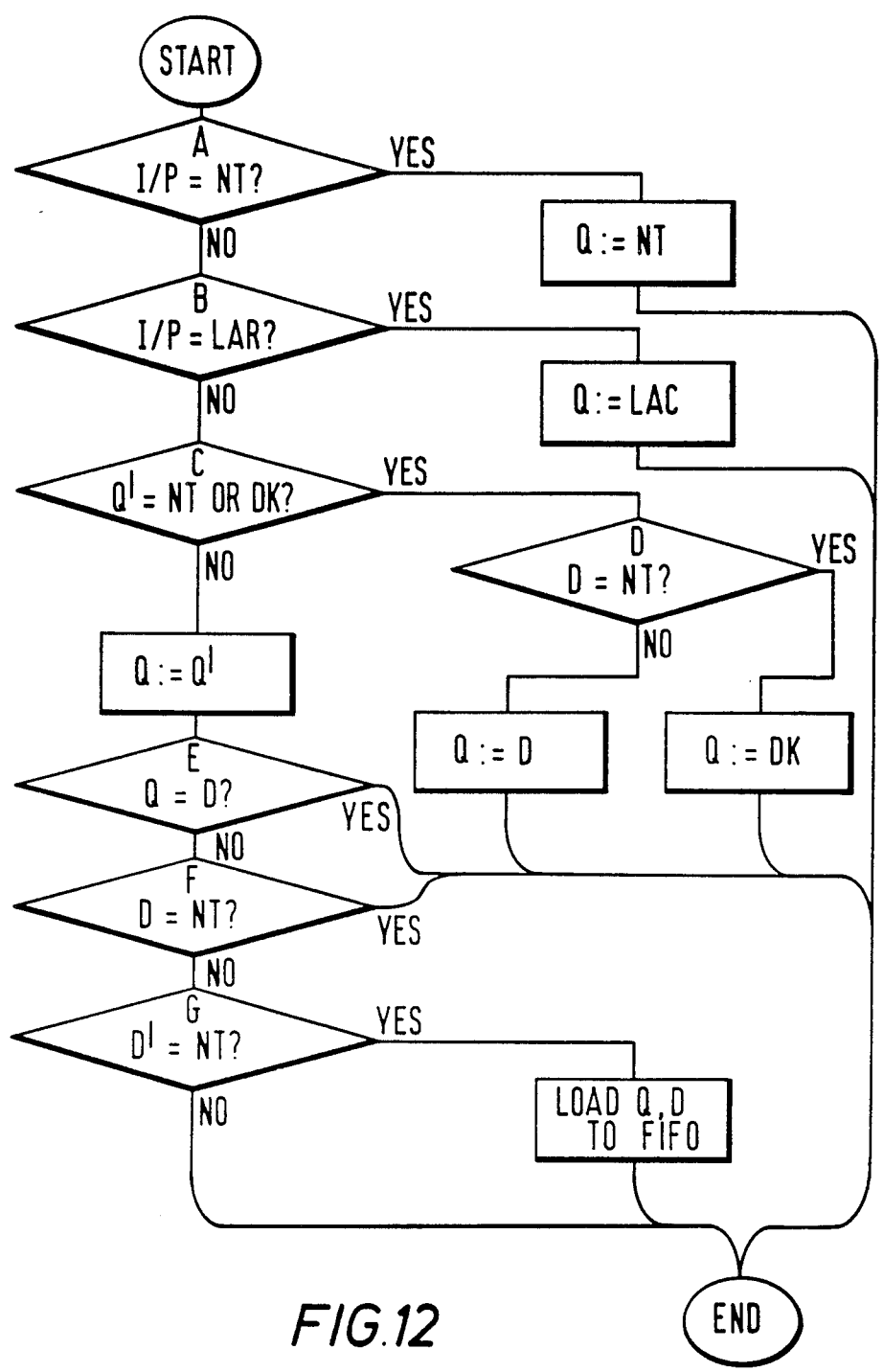
FIGS. 12 and 13 are flow charts illustrating part of the operation of an interconnection analyser.

The logic of the left-right traversal is shown in the flow chart of FIG. 12. Non-track elements are labelled with 'non-track' code. If a 'label allocation request' code is encountered, a new label is obtained from the label allocation counter (FIG. 16). Other elements are labelled by reference to the adjacent elements. In the situations shown below the element marked ? is a track element which is to be labelled, L1 & L2 are differing labels and a 0 represents a non-track element. The various possibilities are as follows:

| L1 | ? |
|----|---|
|    | 0 |

LABEL IS L1

| 0 | ? |
|---|---|
|   | L2 |

LABEL IS L2

-continued

| 0 | ? |
|---|---|
|   | 0 |

LABEL IS 'DON'T KNOW'

| L1 | ? |
|----|---|
|    | L1 |

LABEL IS L1

| L1 | ? |
|----|---|
| 0  | L2 |

LABEL IS L1. COLLISION BETWEEN L1 & L2 MUST BE REPORTED TO THE MICROPROCESSOR

| L1 | ? |
|----|---|
| L2 | L2 |

LABEL IS L1. COLLISION BETWEEN L1 & L2 HAS ALREADY BEEN REPORTED TO THE MICROPROCESSOR

The flowchart of FIG. 12 represents the logical paths which must be followed to obtain these results, where the corresponding symbols are:

| Q' | Q |
|----|---|
| D' | D | when
Q is the name of the box to be filled in.
Q' is the name of the box in the same scan line as Q but 1 place to the left.
D is the name of the box underneath Q. i.e. in the last scan line.
D' is the name of the box underneath Q'. i.e. in the last scan line.
I/P is the input from the bidirectional shift registers in the Label Allocation Request Generator.
NT is the code for 'Non-Track'.
LAR is the code for 'Label Allocation Request'.
DK is the code for 'Don't know'
LAC is the output of the Label Allocation Counter.

Referring to FIGS. 16 and 12, data input is coupled to input 90 and label allocation request input is coupled to input 92 of a control logic circuit 94.

Figure 15:
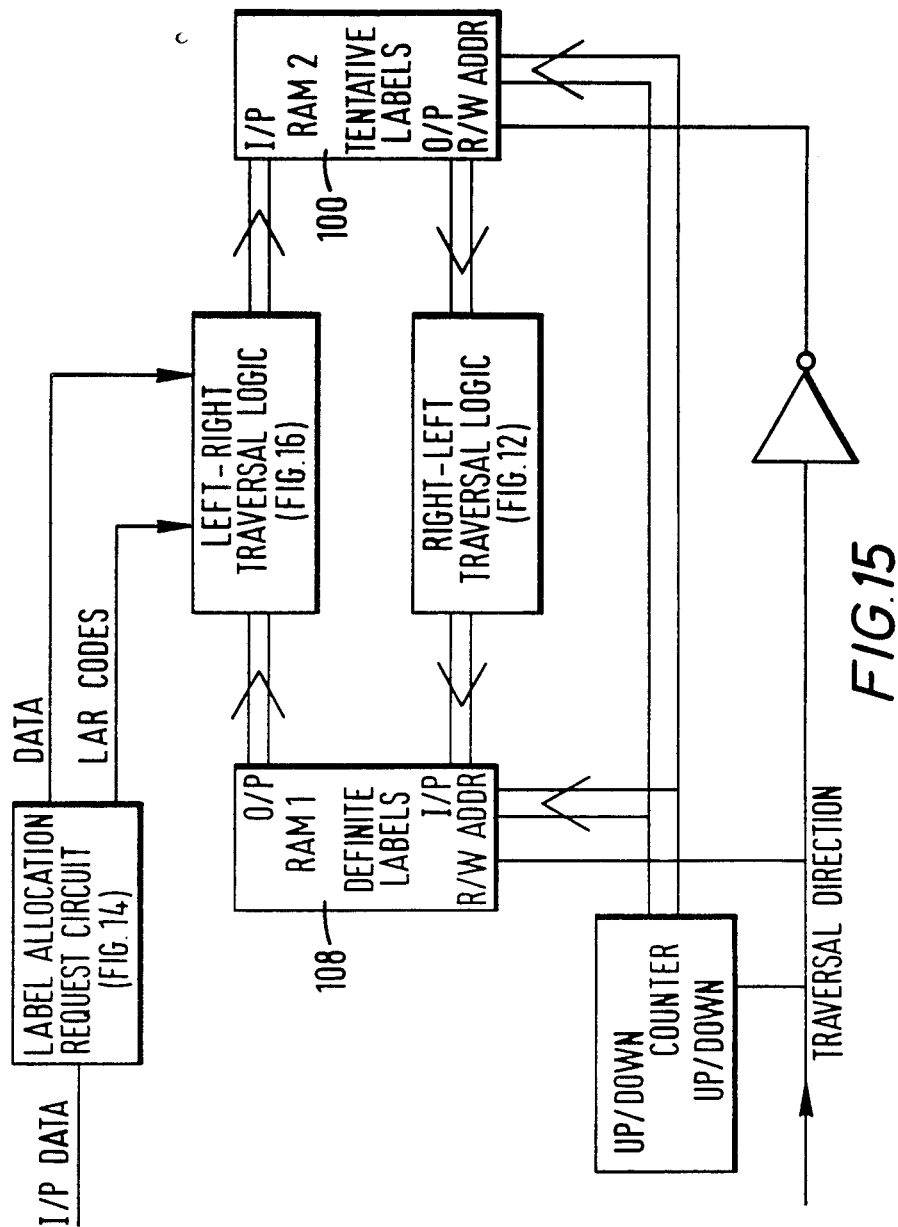
FIG. 15 is a block circuit diagram of an interconnection analyser.

In FIG. 12 each bit of data is interrogated to enquire if it is track or non-track (NT); interrogation (A) if it is NT the action is allocate Q=NT and in FIG. 16 this is achieved by way of the control logic 94 which sets a five way data selector 96 to couple a 16-bit non-track code from circuit 98 to the input of RAM 100 (FIG. 15).

If the input is track then it is interrogated (B) to determine whether there is also a label allocation request signal on input 92. If there is, the logic circuit 94 couples the output of a label allocation counter 102 to the RAM 100, and then increments the counter 102 to the next label address.

If there is not a label allocation request the flow chart enquires whether Q', the Q in the previously interrogated area is non-track (C). If Q' was track then Q is a continuation of the track and the label allocated to Q' must also be allocated to Q. This is achieved by coupling the output of a delay register 104 which is holding Q' to the RAM 100 by way of the data selector 96. If Q' was non-track, the interrogation is, was D non-track (D). If it was NT then it is not yet possible to allocate an address label to Q and it is therefore allocated a 'Don't Know' code from circuit 106. As before the 'Don't Know' code is coupled to RAM 100 by way of data selector 96. If D was track, then Q is allocated the same label as D (Q=D) and the appropriate D label is taken from RAM 108 by way of data selector 96 to RAM 100.

Figure 13:
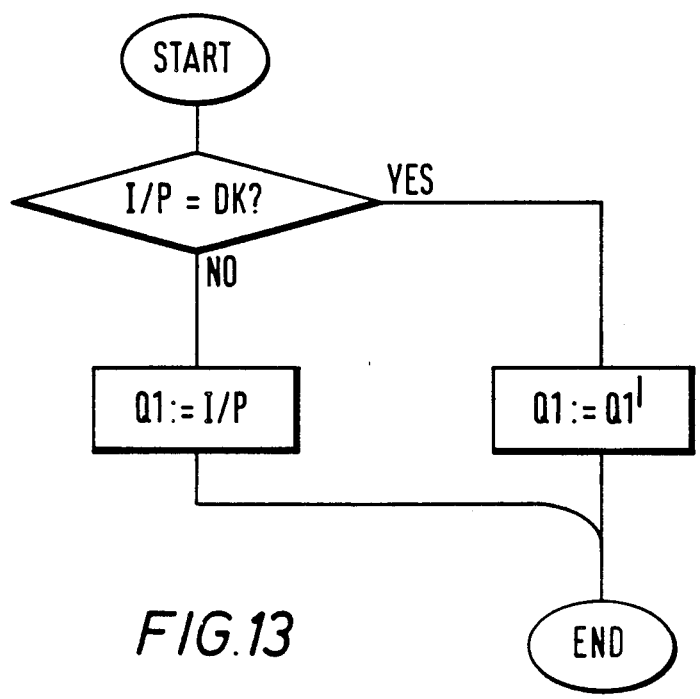

If Q is track and Q' is track (interrogation C) and Q was made equal to Q' then the next interrogation is, does Q=D (interrogation E) if it does then no further action is necessary (Q having been correctly labelled). If however Q is not equal to D then the next question (interogation F) is, is D=NT (non-track) if it is then again no further action is necessary (Q having been correctly labelled). If however D is track and not equal to Q then there is a situation in which both Q and D are track elements which have been allocated different labels although they are in fact touching. This is termed a "collision" in this specification and is detected by comparator 113. It is necessary to report this collision to the microprocessor 14. To save storage space in the computer it is only necessary to report the first instance of a collision and so the next interrogation (G) is, is D'=NT if it is then this must be the first instance of this collision and the control circuitry will then load the label Q and the label D to the microprocessor 14 via the FIFO store 114. If D' is equal to track then the collision must have been reported previously and therefore no further action is necessary. Such a collision is illustrated at position 19 from the left in FIG. 10 where labels 46 and 31 have been allocated to the same piece of track. During the third traversal FIG. 11, the labels are read out from RAM 100 and any 'Don't Knows' are set to the same label as the element on their right by the 'right-left traversal circuit' FIG. 17 before they are written back into RAM 108, in accordance with the flowchart of FIG. 13. Such a 'Don't Know' was shown at position 6 from the left in FIG. 10 and in FIG. 11 it will be seen that it has been allocated label 35. The corresponding symbols for this flowchart are reversed, so that Q1' is the name of the box in the same scan line as Q1 but one place to the right.

| Q1 | Q1' |
|---|---|
| D1 | D1' |

The interconnection analysers 40 and 56 operate in a similar way to that of the analyser 54 but the data input in the case of analyser 56 is, in effect, the data after "track expansion" as hereinbefore described and in the case of analyser 40 it is unmodified data.

Figure 18:
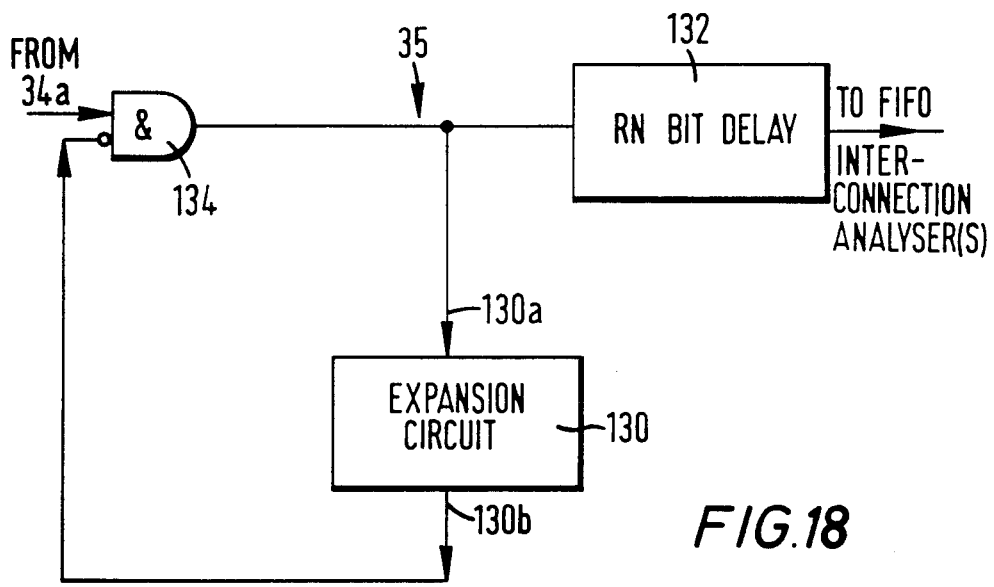
FIG. 18 is a block diagram of a hole detection circuit.
Figure 17:
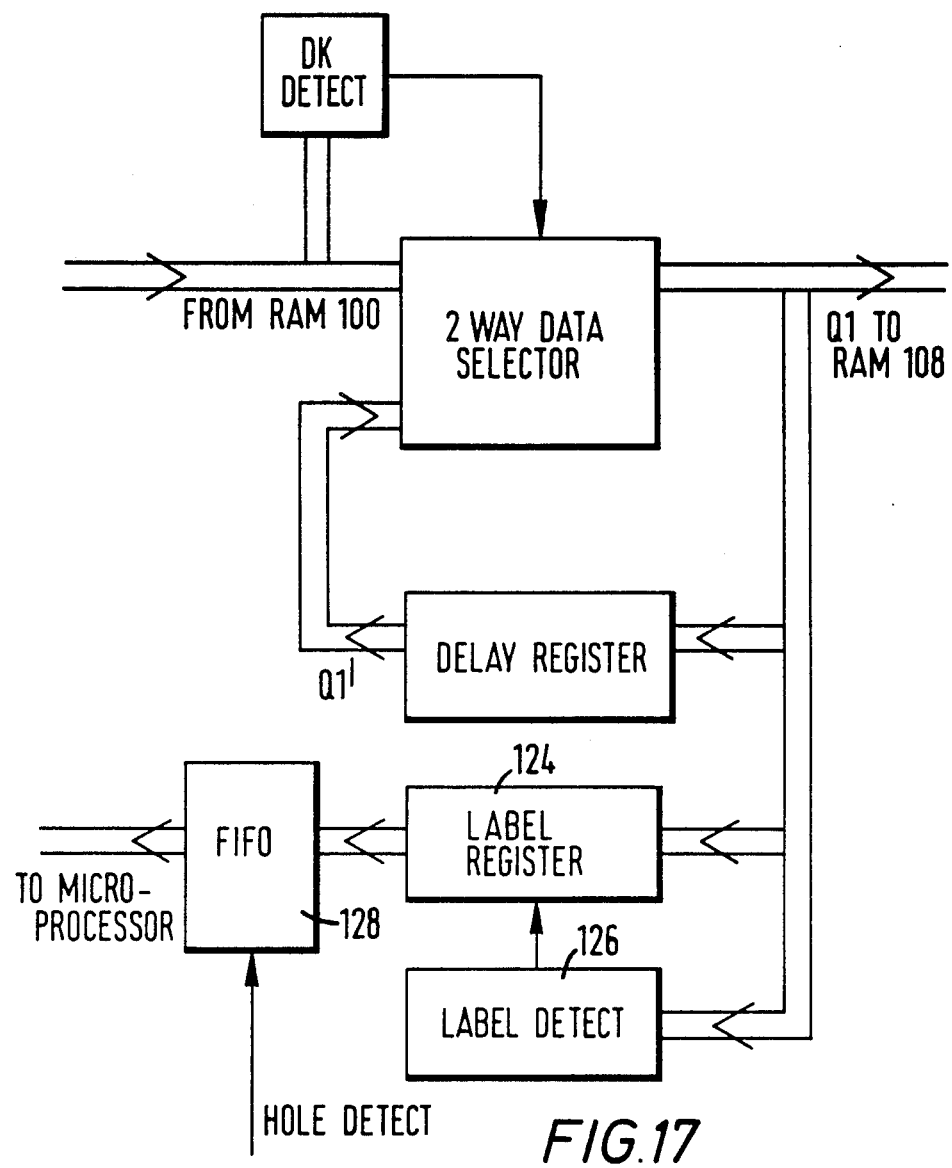

The function of the hole detection circuit 35 FIG. 18 is to generate a single pulse when the input data stream from threshold circuit 34 FIG. 1 corresponds to the centre of a hole in the board 12. Since this hole appears to the threshold circuit as a non-track area, there will be no label corresponding to the centre of the hole. An additional register 124 FIG. 17 is therefore provided which is connected to the output of the interconnection analyser but is clocked only when the label detect circuit 126 detects a label. This register will therefore contain the last label before the hole was encountered and this label is sent via the FIFO buffer 128 FIG. 17 to the microprocessor 14 together with the hole coordinates when the hole detection circuit 35 generates a pulse.

The hole detection circuit is shown in FIG. 18. The 'expansion circuit' 130 shown in this figure is identical to that used for track expansion, and is set to a radius R' slightly greater than the nominal hole size. initially it's input and output signals are both zero. When a hole is first encountered in the input data stream, a single 1 bit is generated at the input 130a to the expansion circuitry 130. The output 130b from the expansion circuit 130 will correspond to a circle slightly larger than the hole, and centered on it. This output is inverted and gated with the input signal at AND gate 134, and therefore serves to suppress all further signals generated by that hole. The single one bit that was generated when the hole was first encountered is delayed in the Rn bit delay 132 to bring it to the centre of the hole, and passed to the interconnection analysers 40,54 and 56.

The information fed to the microprocessor from the interconnection analyser 40 via the FIFO buffer 120 is sufficient to enable a wiring list to be generated indicating which holes are connected to which other holes, and this can be compared with the wiring list obtained from a known good board so that differences between the two can be indicated to the operator in the same way as with a 'bed-of-nails' tester. The wiring lists obtained for the 'thinned' and 'fattened' images by way of analysers 54 and 56 and their respective FIFO buffers 114 and 122 can also be compared to determine the presence of partial breaks and shorts.

A procedure for determining the wiring list is as follows:

(1) Scan a known good board and read the contents of the FIFO buffers into a pair of store tables called REFHOLES and REFCOLLISIONS in the microcomputer. Each entry in the table REFHOLES contains the coordinates of a hole and the label of the adjacent track. Each entry in the table REFCOLLISIONS contains two labels corresponding to two pieces of track that have been found to be touching.

(2) Scan the board under test and read the contents of the FIFO buffers into a corresponding pair of tables called TESTHOLES and TESTCOLLISIONS. Because of minor differences between the two boards, these tables will not necessarily be identical to REFHOLES and REFCOLLISIONS even if the interconnection patterns of the boards are identical.

(3) For each entry in TESTHOLES, read all the entries in REFHOLES to determine which entry has the closest cooordinates. Provided that the boards have been aligned to better than 1.25 mm, this will give the entry for the corresponding hole in the reference board. Replace the coordinates of the entry in TESTHOLES with those for the corresponding entry in REFHOLES, so that corresponding holes now have identical coordinates rather than just very similar ones.

Steps 4-8 are repeated for every entry in TESTHOLES:

(4) Read the label associated with this particular entry in TESTHOLES, and enter it as the only entry in a storage table called TESTLABELS.

(5) Examine all the entries in TESTCOLLISIONS and search for labels which are present in both TESTLABELS and TESTCOLLISIONS. When one is found, compare the label which is associated with that label in TESTCOLLISIONS to the list of labels in TESTLABELS to determine whether it is already present in TESTLABELS. If not, add it to TESTLABELS.

Repeat this procedure until a complete scan of all the entries in TESTCOLLISIONS fails to find any new labels that are not already present in TESTLABELS. TESTLABELS will now contain the labels for all those areas of track that are physically connected together to the hole under consideration.

(6) For each entry in TESTLABELS, examine every entry in TESTHOLES to find labels which are present in both tables. When such a label is found, append the coordinates of the entry in TESTHOLES to an initially empty list called TESTCOORDS.

(7) Sort the entries in TESTCOORDS so that values with smaller X coordinates always appear before values with greater X coordinates. For entries with equal X coordinates, sort them so that values with smaller Y coordinates always appear before values with greater Y coordinates. Standard programs for performing this sorting are available.

(8) Repeat steps 4–7 for the corresponding entry in REFHOLES, using a table REFLABELS in an identical fashion to generate a similar sorted list called REFCOORDS. If the interconnection patterns of the two boards are identical these tables will be identical. Any discrepancy can be reported to the operator as indicating a fault.

We claim:

1. Apparatus for testing a printed wiring board comprising means for optically scanning a board to be tested in two orthogonal, X-Y axes such that for each scan in the Y direction it scans a narrow strip of the board of predetermined width w in the X direction, the scanning means being arranged to provide n.m discrete signals for each scan in the Y direction, wherein n is a predetermined number of signals representative of characteristics of the board across the width w of the strip and m is a number dependent upon the dimension of the board to be scanned in the Y direction such that the n.m signals are representative of the characteristics of the board at the corresponding n.m positions along the strip, and processing means for processing the signals in groups of $n' \times m'$ where $n'$ is less than or equal to n and $m'$ is less than or equal to m to provide signals representative of the characteristics of the board along said strip and means for storing said signals, control means arranged to cause the scanning means repeatedly to scan the board in the Y direction and to step the scanned strip a predetermined amount in the X direction at the end of each scan until a required area of the board has been scanned and the processing means has processed a plurality of said groups of signals, the processing means being further arranged to identify common areas of each conductive track such that at the completion of a test, the storage means contains information representative of the X-Y coordinates of a plurality of datum areas and of the ones of said datum areas which are interconnected.

2. Apparatus according to claim 1, wherein the processing means comprises means for comparing the stored signals with a plurality of signals representative of the required interconnections for the board (the required wiring list) thereby to test the quality of the board.

3. Apparatus according to claim 2, wherein the optical scanning means is arranged to generate a series m of output signals as the board is scanned in the Y direction, each output signal comprising n analogue information signals representative of the said characteristics of the board across the width w of the strip.

4. Apparatus according to claim 3, wherein the n analogue information signals are coupled serially to the input of threshold circuit means arranged to determine from each information signal the characteristics of the board at the position on the board corresponding to the information signal and to provide a first digital signal representative of track, a second digital signal representative of non-track or a third digital output signal representative of a datum area such as a hole.

5. Apparatus according to claim 4, wherein the processing means comprises temporary storage means having an input arranged to receive and store said digital signals representative of track or non-track, said temporary storage means having $m'$ parallel outputs, whereby at any instant in time the output of the storage means is representative of the characteristics of the board in a row $m'$-bits long in the Y direction of scan.

6. Apparatus according to claim 5 wherein the control means includes a digital clock arranged to synchronise operation of the apparatus, the analogue information signals are coupled to the threshold circuit at clock rate and the stored digital signals are presented sequentially to the outputs of the temporary storage means at clock rate whereby for a given n clock pulses the output of the storage means is representative of a parallel scan across the width w of the board.

7. Apparatus according to claim 6, wherein the processing means comprises track contraction means for processing preselected areas of each group of $n' \times m'$ signals in such a manner as to determine whether the width of a conductor at any point along its length is less than or greater than a predetermined minimum width and to provide an output indicative thereof.

8. Apparatus according to claim 7, wherein the track contraction means comprises a plurality $m'$ of tapped $n'$-bit shift registers each having an input coupled to a corresponding output of the temporary storage means and a programmable, tapped output coupled to a preset input of a corresponding presettable down counter, whereby at a given interval of time the shift registers contain digital information representative of an area of the board $n' \times m'$ where n and m are dimensions in the X and Y directions respectively.

9. Apparatus according to claim 8, wherein the positions of the taps on said tapped shift registers are controlled by a microprocessor in said processing means and are set to select from the shift registers the outputs of individual stages thereof which lie within a circle of radius R in the area $n' \times m'$, where R is dependent upon the minimum required width of the track, such as half the track width.

10. Apparatus according to claim 9, wherein the taps on the shift registers are set such that on the first and $m'$th shift registers the tap is arranged to select a minimum number of stages centered on the $n'/2$ stage, the tap on the $m'/2$ shift register is set to select a maximum number of its stages, the taps on the second to the $(m'/2-1)$ stage are arranged to select an increasing number of stages between the said minimum and maximum number and the taps on the $(m'/2+1)$ to the $(m'-1)$ stage are set to select a decreasing number of stages between the said maximum and minimum numbers.

11. Apparatus according to claim 8, wherein the presettable down counters are set to a count equal to the number of selected stages in its corresponding shift register.

12. Apparatus according to claim 11, wherein the outputs of the down counters are coupled to gate means arranged to provide an output indicative of track only if all of the selected stages of the shift registers contain digital information indicative of track.

13. Apparatus according to claim 12, wherein the output of the track contraction means is coupled to an input of first interconnection analyser means arranged to determine which datum areas are connected together and to provide output information to a storage means, the output information being stored as a wiring list of datum areas interconnected by track of width equal to or greater than the said minimum specified track width.

14. Apparatus according to claim 1, wherein the processing means comprises track contraction means for processing preselected areas of each group of $n' \times m'$ signals in such a manner as to determine whether the width of a conductor at any point along its length is less than or greater than a predetermined minimum width and to provide an output indicative thereof.

15. Apparatus according to claim 14, wherein the output of the track contraction means is coupled to an input of first interconnection analyser means arranged to determine which datum areas are connected together and to provide output information to a storage means, the output information being stored as a wiring list of datum areas interconnected by track of width equal to or greater than the said minimum specified track width.

16. Apparatus according to claim 15, wherein the output of the track contraction means in n-bit serial form representative of track or non-track is coupled to the input of a label allocation request circuit in the interconnection analyser means arranged to identify each discrete area of track and allocate a label thereto from a label counter, the X-Y coordinates of each datum area and its associated label being coupled to a storage means, such that at the end of a test, the labels and X-Y coordinates of the datum areas are stored in said storage means as a wiring list of interconnected datum areas.

17. Apparatus according to claim 16, wherein the interconnection analyser comprises means for determining when two tracks having different labels converge and for coupling an information signal to the storage means that the said tracks are interconnected.

18. Apparatus according to claim 17, wherein the label allocation request circuit is arranged to scan said n bits of information in a scan line a plurality of times; in a first scan in one direction the circuit is arranged to identify each region of track which does not touch a region of track in the immediately preceding scan line to provide a label allocation request (LAR) signal in the first non-track area after the identified track region such that at the end of the first scan a data store contains the n-bits of scanned information and a label allocation request store contains the LAR signal in the said first non-track area; in the second scan in an opposite direction, an LAR signal from the LAR store is coupled to the label allocation counter which couples a label address to the corresponding identified track region in the n-bit scan line and is updated one count, other unlabelled track areas are provided with label addresses corresponding to the addresses of adjacent track areas, and remaining unlabelled track areas are allocated a "dont know[ code; and in the third scan areas previously allocated a "dont know" code are provided with a label address corresponding to that in the immediately preceding area.

19. Apparatus according to claim 18, wherein the processing means comprises track expansion means for processing the scan signals in such a manner as to determine whether the spacing between adjacent tracks at any point along their length is less than a predetermined value and to provide an output indication thereof.

20. Apparatus according to claim 18, wherein the digital information comprising the wiring list in the storage means coupled to the output of the first interconnection analyser means is compared under the control of the microprocessor with digital information corresponding to a required wiring list to determine whether the board under test is within acceptable limits as to track widths.

21. Apparatus according to claim 20, wherein the digital information comprising the wiring list in the storage means coupled to the output of the second interconnection analyser means is compared under the control of the microprocessor with digital information corresponding to a required wiring list to determine whether the board under test is within acceptable limits as to track spacings.

22. Apparatus according to claim 15, wherein the digital information comprising the wiring list in the storage means coupled to the output of the first interconnection analyser means is compared under the control of the microprocessor with digital information corresponding to a required wiring list to determine whether the board under test is within acceptable limits as to track widths.

23. Apparatus according to claim 22 and the digital information comprising the wiring list in the storage means coupled to the output of the second interconnection analyser means is compared under the control of the microprocessor with digital information corresponding to a required wiring list to determine whether the board under test is within acceptable limits as to track spacings.

24. Apparatus according to claim 22, wherein the required wiring list is derived from a photographic or other artwork prepared for the board or from a known good board.

25. Apparatus according to claim 22, wherein the processing means comprises a third interconnection analyser means having its input coupled to the output of the temporary storage means and its output coupled to a storage means thereby to store a basic wiring diagram of the board irrespective of the width of and spacing between tracks.

26. Apparatus according to claim 25, wherein the required wiring list is derived from the storage means coupled to the third interconnection analyser means.

27. Apparatus according to claim 15, wherein the processing means further comprises hole detection circuit means having an input coupled to the output of said threshold circuit means and an output coupled to the input of the interconnection analyser means, the hole detection circuit means being arranged to generate a 'hole' output signal when the digital data signals from the threshold circuit correspond to the centre of a hole in the track on the board, and the storage means coupled to the interconnection analyser means is arranged to store the X-Y coordinate of each hole and the label of the track surrounding the hole.

28. Apparatus according to claim 14, wherein the processing means comprises track expansion means for processing the scan signals in such a manner as to determine whether the spacing between adjacent tracks at any point along their length is less than a predetermined value and to provide an output indication thereof.

29. Apparatus according to claim 28, wherein the track expansion means comprises a plurality m' of tapped n'-bit shift registers each having an input coupled to a corresponding output of the temperary storage means and a programmable, taped output coupled to a preset input of a corresponding presettable down counter, whereby at a given interval of time the shift registers contain digital information representative of an area of the board n'×m' where n and m are dimensions in the X and Y directions respectively and wherein the input of each shift register is coupled to an inverted output of the said temporary storage means such that in the track expansion means areas of track and non-track on the board are treated as non-track and track respectively, and the value of R is dependent upon the minimum required spacing between adjacent tracks, such as half the minimum track spacing.

30. Apparatus according to claim 29, wherein the output of the track expansion means is coupled to an input of a second interconnection analyser means arranged to determine which datum areas are connected together and to provide output information to a storage means, the output information being stored as a wiring list of datum areas interconnected by track, in which the spacing between adjacent tracks at any point along their length is equal to or greater than the said predetermined value.

31. Apparatus according to claim 30, wherein the output of the track expansion means in n-bit serial form representative of track or non-track is coupled to the input of a label allocation request circuit in the second interconnection analyser means arranged to identify each discrete area of track and allocate a label thereto from a label counter, the X-Y coordinates of each datum area and its associated label being coupled to a storage means, such that at the end of a test, the labels and X-Y coordinates of the datum areas are stored in said storage means as a wiring list of the interconnected datum areas.

32. Apparatus according to claim 31, wherein the interconnection analyser comprises means for determining when two tracks having different labels converge and for coupling an information signal to the storage means that the said tracks are interconnected.

33. Apparatus according to claim 32, wherein the label allocation request circuit is arranged to scan said n bits of information in a scan line a plurality of times; in a first scan in one direction the circuit is arranged to identify each region of track which does not touch a region of track in the immediately preceding scan line to provide a label allocation request (LAR) signal in the first non-track area after the identified track region such that at the end of the first scan a data store contains the n-bits of scanned information and a label allocation request store contains the LAR signal in the said first non-track area, in the second scan in an opposite direction, an LAR signal from the LAR store is coupled to a label allocation counter which couples a label address to the corresponding identified track region in the n-bit scan line and is updated one count, other unlabelled track areas are provided with label addresses corresponding to the addresses of adjacent track areas, and remaining unlabelled track areas are allocated a "dont know" code; and in the third scan areas previously allocated a "dont know" code are provided with a label address corresponding to that in the immediately preceding area.

34. Apparatus according to claim 28, wherein the output of the track expansion means is coupled to an input of a second interconnection analyser means arranged to determine which datum areas are connected together and to provide output information to a storage means, the output information being stored as a wiring list of datum areas interconnected by track, in which the spacing between adjacent tracks at any point along their length is equal to or greater than the said predetermined value.

35. Apparatus according to claim 28, wherein the digital information comprising the wiring list in the storage means coupled to the output of the second interconnection analyser means is compared under the control of the microprocessor with digital information corresponding to a required wiring list to determine whether the board under test is within acceptable limits both as to track positions and spacings.

36. Apparatus according to claim 1, further comprising display means coupled to an output of said microprocessor for displaying the results of said tests.

37. Apparatus according to claim 1, further comprising display means coupled to an output of said microprocessor for displaying the results of said tests.

38. A process for testing a printed wiring board comprising the steps of optically scanning a board to be tested in two orthogonal, X-Y axes such that for each scan in the Y-direction a narrow strip of predetermined width, w, in the X direction is scanned, deriving n.m discrete signals for each scan in the Y direction, wherein n is a predetermined number of signals representative of characteristics of the board across the width w of the strip and m is a number dependent upon the dimension of the board being scanned in the Y direction, and digitally processing the signals in groups of n'×m' where n' is less than or equal to n and m' is less than or equal to m to provide signals representative of the characteristics of the board along said strip and storing said signals, scanning the board repeatedly in the Y direction and stepping it a predetermined amount in the X direction at the end of each scan until a required area of the board has been scanned and a plurality of said groups of signals has been processed, and identifying common areas of each conductive track such that at the completion of a test, information representative of the X-Y coordinates of a plurality of datum areas and of the said datum areas which are interconnected are stored as a wiring list.

* * * * *